US010572706B2

(12) United States Patent
Schneider et al.

(10) Patent No.: US 10,572,706 B2
(45) Date of Patent: Feb. 25, 2020

(54) REFLEX LONGITUDINAL IMAGING USING THROUGH SENSOR INSONIFICATION

(71) Applicant: QUALCOMM Incorporated, San Diego, CA (US)

(72) Inventors: John Keith Schneider, Williamsville, NY (US); Jack Conway Kitchens, II, Town of Tonawanda, NY (US)

(73) Assignee: Qualcomm Incorporated, San Diego, CA (US)

( * ) Notice: Subject to any disclaimer, the term of this patent is extended or adjusted under 35 U.S.C. 154(b) by 189 days.

(21) Appl. No.: 15/414,992

(22) Filed: Jan. 25, 2017

(65) Prior Publication Data

US 2017/0132446 A1 May 11, 2017

Related U.S. Application Data

(63) Continuation of application No. 13/105,065, filed on May 11, 2011, now abandoned.

(60) Provisional application No. 61/333,304, filed on May 11, 2010.

(51) Int. Cl.
| | |
|---|---|
| *G06K 9/00* | (2006.01) |
| *A61B 5/1172* | (2016.01) |
| *G01S 15/89* | (2006.01) |
| *G01S 15/18* | (2006.01) |

(52) U.S. Cl.
CPC .......... *G06K 9/0002* (2013.01); *A61B 5/1172* (2013.01); *G01S 15/8913* (2013.01); *G01S 15/18* (2013.01)

(58) Field of Classification Search
CPC ... A61B 5/1172; G01S 15/18; G01S 15/8913; G06K 9/0002
See application file for complete search history.

(56) References Cited

U.S. PATENT DOCUMENTS

| | | |
|---|---|---|
| 4,385,831 A | 5/1983 | Ruell |
| 4,730,495 A | 3/1988 | Green |
| 4,977,601 A | 12/1990 | Bicz |
| 5,218,644 A | 6/1993 | Bauer |
| 5,258,922 A | 11/1993 | Grill |

(Continued)

OTHER PUBLICATIONS

International Search Report and Written Opinion—PCT/US2011/036006—ISA/EPO—dated Aug. 12, 2011.

(Continued)

*Primary Examiner* — Francis Geroleo
(74) *Attorney, Agent, or Firm* — Weaver Austin Villeneuve & Sampson LLP

(57) ABSTRACT

An ultrasonic reflex imaging device and a method are described. A device according to the invention may include a platen, a generator, and a receiver positioned between the platen and the generator. A backer may be positioned so that the insonification device is between the receiver array and the backer. The backer may be configured to absorb or delay energy that originated from the generator. The generator produces an energy pulse, which travels through the receiver and the platen to reach a biological object. Part of the energy pulse is reflected from the biological object. The reflected energy pulse travels through the platen to the detector. The detector converts the reflect energy pulse to electric signals, which are then interpreted to create an image of the biological object.

19 Claims, 3 Drawing Sheets

(56) References Cited

U.S. PATENT DOCUMENTS

| | | | |
|---|---|---|---|
| 5,486,734 | A | 1/1996 | Seyed-Bolorforosh |
| 5,515,298 | A | 5/1996 | Bicz |
| 5,589,636 | A | 12/1996 | Bicz |
| 5,828,627 | A | 10/1998 | Bicz |
| 6,175,641 | B1 | 1/2001 | Kallo et al. |
| 7,358,515 | B2 | 4/2008 | Setlak et al. |
| 7,400,750 | B2 | 7/2008 | Nam |
| 2003/0067249 | A1 | 4/2003 | Lockwood et al. |
| 2005/0265586 | A1 | 12/2005 | Rowe et al. |
| 2007/0272020 | A1 | 11/2007 | Schneider et al. |
| 2008/0258580 | A1 | 10/2008 | Schneider et al. |
| 2011/0178407 | A1* | 7/2011 | Lu ........................ A61B 8/4281 600/459 |
| 2011/0279662 | A1 | 11/2011 | Schneider et al. |

OTHER PUBLICATIONS

U.S. Office Action dated Aug. 29, 2013 issued in U.S. Appl. No. 13/105,065.

U.S. Final Office Action dated Dec. 31, 2013 issued in U.S. Appl. No. 13/105,065.

U.S. Office Action dated Jun. 3, 2014 issued in U.S. Appl. No. 13/105,065.

U.S. Final Office Action dated Oct. 10, 2014 issued in U.S. Appl. No. 13/105,065.

\* cited by examiner

REFLEX LONGITUDINAL IMAGING USING THROUGH SENSOR INSONIFICATION

PRIORITY DATA

This patent document is a continuation of and claims priority to co-pending and commonly assigned U.S. patent application Ser. No. 13/105,065, filed on May 11, 2011, which claims priority to U.S. Provisional Patent Application No. 61/333,304, filed on May 11, 2010. The entire disclosures of U.S. patent application Ser. No. 13/105,065 and U.S. Provisional Patent Application No. 61/333,304 are hereby incorporated by reference for all purposes.

FIELD OF THE INVENTION

The present invention relates to a system for gathering information that can be used to create an image of an object. The information is obtained using a longitudinal wave, such as an ultrasound wave.

BACKGROUND OF THE INVENTION

Since the 1800's fingerprint information has been collected from human fingers and hands by means of ink and paper. For the purposes of this invention, the term fingerprint refers to the skin surface friction ridge detail of a single digit, or part of the friction ridge detail of a digit, or any portion of the skin surface friction ridge up to and including the entire hand. In recent years, various electronic fingerprint scanning systems have been developed utilizing optical, capacitance, direct pressure, thermal, and longitudinal-wave methods. Methods based upon longitudinal waves, including ultrasound, have proven to be highly accurate, since longitudinal waves are unaffected by grease, dirt, paint, ink and other substances commonly found on a person's skin.

Use of ultrasound typically employs a piezoelectric transducer to send an ultrasonic energy wave, often referred to as a pulse, through a transmitting media. The pulse partially reflects back at each interface between media. The reflected portion of the pulse can be used to determine the distance traveled by the pulse, and this can be done for each partially reflecting interface. However, not all of the reflected pulses are of interest. For example, when a fingerprint is of interest, the pulse reflected by interfaces other than where the finger resides are not of interest. Since pulses reflected by the various interfaces will arrive at different times, it is possible to identify those pulses that are of interest by monitoring a time interval during which the reflected pulse for that interface is expected to arrive. This process is often referred to as range gating or biasing. The reflected pulse received during the expected time is then processed, often by converting it to digital values that represent signal strength. Through a single pixel sweep scanning device, information from a reflected pulse can be graphically displayed as a three-dimensional contour map of the object of a human finger, thumb or other skin surface. With respect to interface surfaces that are not flat, the depth of any gap structure detail (e.g. fingerprint valleys) can be displayed as a gray-scale bitmap image.

Although ultrasound imaging of a fingerprint is superior in detail to a similar image collected by an optical system or other means, we have discovered an arrangement of components which provides a superior image.

SUMMARY OF THE INVENTION

The invention may be embodied as an ultrasonic reflex imaging device. Such a device may include a platen, an insonification device (also known as a generator), and a receiver array positioned between the platen and insonification device. The receiver array may be in physical contact with the platen. A backer may be positioned so that the insonification device is between the receiver array and the backer. The backer may be configured to absorb or delay energy that originated from the generator.

The insonification device may be a plane wave generator. That is to say that the energy generated may be substantially planar. The energy may be in the form of a longitudinal wave, such as an ultrasonic wave.

The platen may include an array of waveguides, or a microlens array. The platen may be suitable for resting a biological object such as a finger while the biological object is analyzed using the longitudinal wave generated by the insonification device.

The invention may be embodied as a method of capturing biometric information from the biological object. In one such method, an ultrasonic pulse emanates from an insonification device, and the pulse travels through a receiver array, before reaching a biological object. Part of the pulse is reflected by the biological object, and the reflected energy is detected and converted to a plurality of electric charges. The electric charges are processed (for example, by a computer) to assemble a digital image representation of the biological object.

BRIEF DESCRIPTION OF THE DRAWINGS

For a fuller understanding of the nature and objects of the invention, reference should be made to the accompanying drawings and the subsequent description. Briefly, the drawings are.

DETAILED DESCRIPTION OF THE INVENTION

Figure 1:
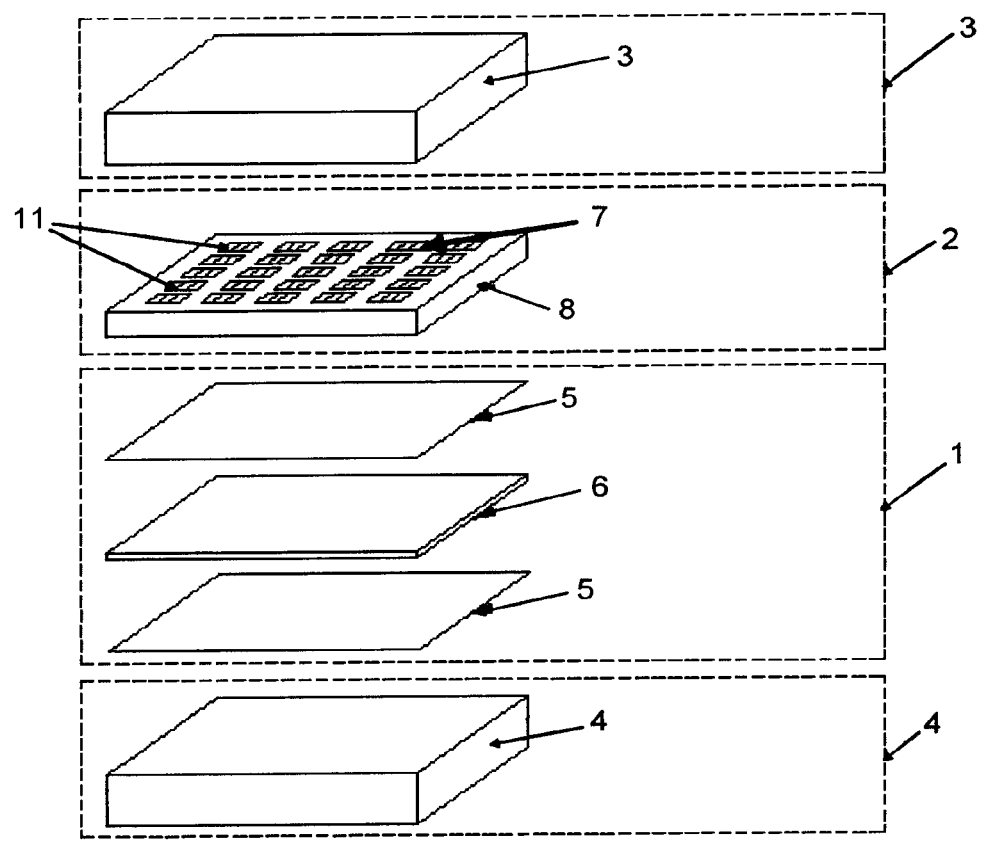
FIG. 1 is an exploded perspective view of one embodiment of a device according to the invention.

The invention described herein is illustrated by way of one or more particular embodiments. Initially, a general overview of the invention is provided, followed by additional details. The invention may be embodied as an ultrasonic reflex imaging device comprising a platen, an insonification device, and an ultrasonic receiver array positioned between the platen and the insonification device. The ultrasonic receiver array may be in physical contact with the platen. The platen may be bonded to the receiver array through an adhesive, such as an epoxy, a two-part acrylic, or a cyanoacrylate super glue. Also, the insonification device may be a plane wave generator. In another embodiment, the imaging device further comprises a backer positioned such that the insonification device is between the receiver array and the backer. The backer may be configured to absorb or delay acoustic signals.

The receiver array can be constructed from a number of suitable materials for receiving ultrasonic pulses. For example, the receiver array can be a thin film transistor array with a piezoelectric sensing layer, a CMOS array with a piezoelectric sensing layer, or a MEMS array with a piezoelectric sensing layer.

The platen may also be constructed in a number of configurations, from a variety of suitable materials. For example, the platen can be a plastic plate. In one embodiment, the platen is an acoustic waveguide array, an example of which is described in U.S. patent application Ser. No. 12/555,220, the disclosure of which is incorporated herein by reference. In another embodiment, the platen is an acoustic microlens array, an example of which is described in U.S. Pat. No. 5,230,990, the disclosure of which is incorporated herein by reference. Microlens arrays can be used to shape, focus, or direct pulses produced by an ultrasonic generator.

In one embodiment, the invention can capture biometric information from a biological object by emitting at least one ultrasonic pulse from an insonification device, such that the pulse travels through a receiver array before reaching a biological object. Upon reaching the biological object, a portion of the ultrasonic pulse is reflected from the biological object and the reflected pulse is detected by the receiver array. The receiver array converts the reflected ultrasonic pulse to a plurality of electric charges, and processes the plurality of electric charges to assemble a digital image representation of the biological object.

The receiver array may include detecting elements that are arranged in a two-dimensional array. A high resolution ultrasound receiver array formed by the detecting elements may be made to work in concert with a physically separate piezoelectric plane wave pulse generator that is capable of emitting an energy wave in the ultrasonic frequency range. Fingerprint image data may be captured by the receiver array. Each detector in the receiver array can produce information corresponding to part of that image. Each detector may be addressable using software such that the image information can be processed and feature manipulated by dedicated devices. In this manner, a fingerprint template can be created locally on the device, using for example an integrated circuit or chip set, thereby relieving a system of the need for subsequent image acquisition processing.

Figure 2:
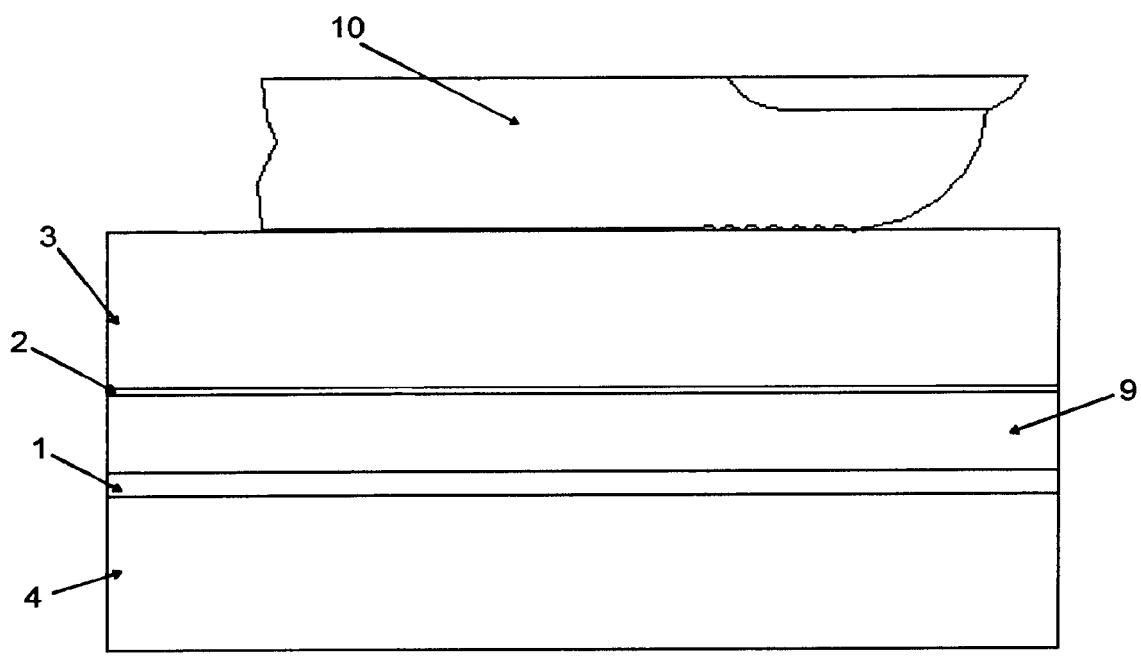
FIG. 2 is an assembled view of the device depicted in FIG. 1.

Having provided a general overview of devices that are in keeping with the invention, additional details are now provided. FIGS. 1 and 2 depict an embodiment of a reflection based (reflex) ultrasonic imaging device 9 having a backer 4 that may absorb or delay ultrasonic energy. The figures also depict an ultrasonic plane wave generator 1, which can be fabricated from a piezoelectric device 6, which can be a film or ceramic element, and metalized electrodes 5 attached to the piezoelectric device 6. Since the piezoelectric device 6 may reside substantially in a plane, the wave generated by the device 6 may emanate in a substantially planar fashion.

A device according to the invention may include an ultrasonic receiver array 2 and a platen 3. The skin of a finger 10 may be applied to the platen 3 for purposes of generating an image of the fingerprint. Once applied to the platen 3, the generator 1 produces an energy wave at an ultrasonic frequency, the energy wave travels through the receiver array 2, through the platen 3, to the finger 10. A portion of the energy wave is reflected by the finger 10, and the reflected energy wave travels through the platen 3 toward the receiver array 2.

The receiver array 2 may include an array 7 of piezoelectric detectors 11 that are sensitive to pressure changes, for example those caused by an ultrasonic pulse. An insulating substrate 8 may be associated with the receiver array 2. The insulating substrate 8 may be constructed from quartz glass or borosilicate glass. The insulating substrate 8 may be made from a material that electrically insulates the receiver array 2 from the generator 1.

The detectors 11 of the array 7 may each be a semiconductor device, which are each addressable by row and column (or another method of identification), and each detector 11 in the array 7 may be thought of as an individual pixel element. For example, the detectors 11 of the array 7 may also each be a thin film transistor device, a CMOS device, or a MEMS device.

The platen 3 may be included to help convey ultrasonic energy to and from the skin that is in contact with the exposed surface of the platen 3. The platen 3 may be a homogeneous plastic plate, a waveguide array, or a microlens array. The advantages of using a waveguide array or microlens array include benefits arising from a finer aperture acoustic energy path between the skin of the finger 10 and the piezoelectric receiver array 2, which will produce a sharper and clearer image of the object that is in contact with the exposed surface of the platen 3.

A reflex imaging device according to the invention may operate in the following manner. An electrical excitation pulse, or series of pulses, may be applied to the plane wave generator 1 which, in turn emits an ultrasonic pulse or series of pulses. The ultrasonic pulse travels through the insulating substrate 8 and the receiver array 2, and then through the platen 3, to the surface of the platen 3 where the finger 10 resides. The pulse is reflected back wherever the fingerprint is not in contact with the platen 3, for example the valleys of the finger's friction surface. Where the platen 3 contacts skin, for example at fingerprint ridges, the acoustic energy is absorbed and/or scattered. The portion of the ultrasonic energy pulse that reflects back carries information about the fingerprint valleys. Areas where there is a relative lack of a reflected signal indicate the locations of the ridges of the fingerprint that contact the platen 3. When the ultrasonic pulse arrives at the ultrasonic receiver array 2, it is converted by the detectors 11 to electric charges, and these may be accessed by row and column using externally controlled electronics. This array of charges is converted from an analog to a digital form by an analog-to-digital converter. The digital form may then be operated upon by applying a fixed pattern offset and gain corrections, which may be previously characterized and stored, and which correspond to and are characteristic of the receiver array 2. The result is a digital image representation of the finger residing on the platen 3.

The backer 4 may be fixed by an adhesive to the ultrasonic plane wave generator 1, for example to the metalized electrode 5. In one embodiment, the backer 4 may absorb parasitic ultrasonic energy from the plane wave generator 1 that might otherwise interfere with ultrasonic pulses reflected from the biological object, or be misinterpreted as ultrasonic pulses reflected from the finger 10. In another embodiment, the backer 4 delays ultrasonic energy such that the delayed ultrasonic energy arrives at the receiver array 2 outside of the expected range gate period. Delayed ultrasonic responses are detected by the receiver array 2, however they can be categorically discarded because they arrive at a distinguishably later time than the pulses that are reflected from the finger 10. A material that may be used as the backer 4 is borosilicate glass. Another material that may be used as the backer 4 is quartz glass. The backer 4 and the platen 3 may be arranged as an integral piece, thereby embedding the receiver array 2 and the plane wave generator 1 between them. The backer 4 may also be made from the same material as the platen 3.

An advantage of placing the plane wave generator 1 outside of the path between the finger 10 and the receiver 2 is that the materials of construction for the piezoelectric element 6 may be either a polymer or a ceramic piezoelectric. Another advantage is that the excitation signal to the generator 1 can be larger and there will be less loss of usable acoustic energy. By way of contrast, the prior art devices that use a single device for both generation and detection require that care be given to the excitation electric signal so as not to damage the sensitive electronic receiver elements. By making the plane wave generator 1 and the receiver 2 different devices, a more robust generator 1 can be employed. Also, a configuration according to the invention reduces the number of interfaces between the finger 10 and the receiver 2, when compared to prior art devices. Reducing the number of interfaces between the receiver 2 and the object being imaged reduces signal loss, since every material interface is a potential source of acoustic reflection.

Physical separation of the ultrasound pulse creation device from the reflected ultrasound pulse detector device allows the ultrasound pulse generation to be optimized without the compromises required of a dual purpose device that serves both to generate and detect. The present invention situates the ultrasonic receiver array between the target and the generator of the ultrasonic pulse. The invention may be configured to permit the use of ultrasonic devices between the generator and the target object in order to allow the ultrasonic energy to be optimally focused or aperture limited for improved image acquisition. Situating the receiver array between the pulse generator and the object to be imaged allows the use of pulse emitting appliances that would not be suitable for other configurations due to the acoustic impedance mismatch between the generator and the other components within the acoustic signal path.

Figure 3:
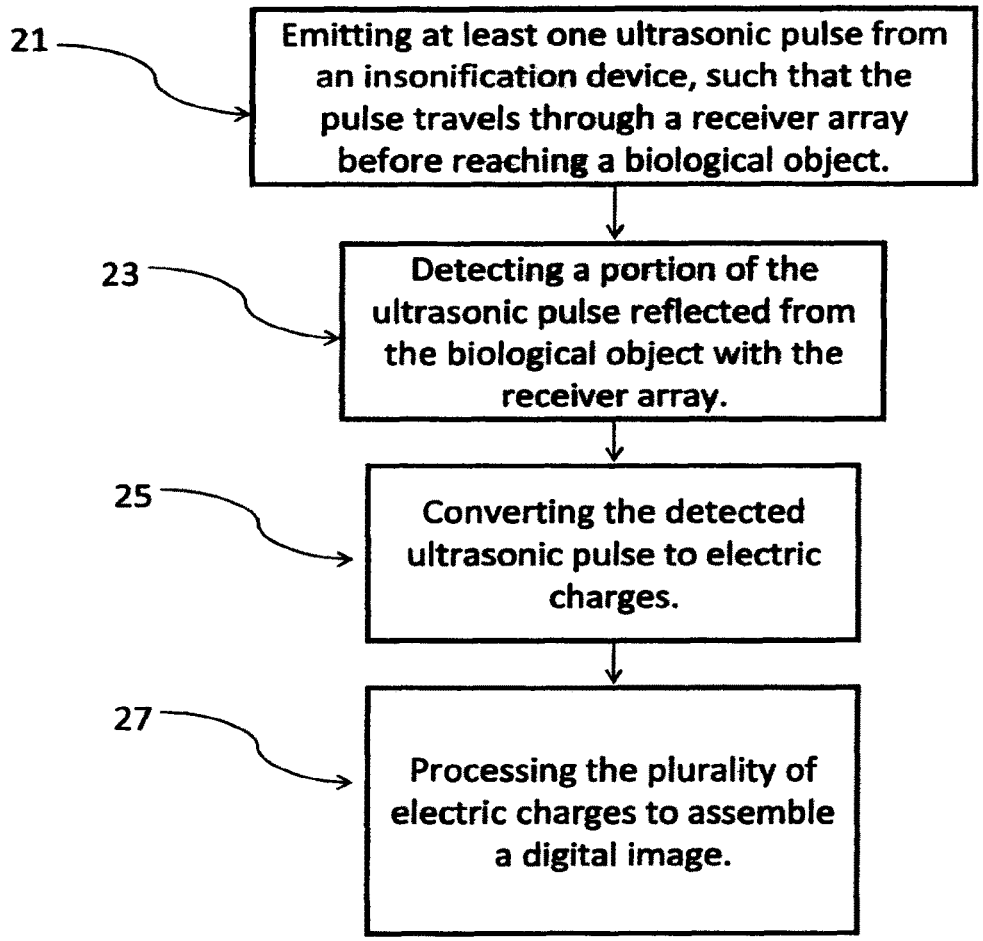
FIG. 3 is a flow chart describing a method according to the invention.

The present invention may also be implemented as a method of capturing biometric information. FIG. 3 depicts one such method in which at least one ultrasonic pulse is emitted 21 from an insonification device, for example, a plane wave generator 1. The pulse travels through a receiver array 2 and reaches a biological object that is resting on a platen 3, for example, a human finger 10. A portion of the ultrasonic pulse is reflected from the finger 10. The reflected pulse travels through the platen 3 and is detected 23 by the receiver array 2. The detected ultrasonic pulse is converted 25 into a plurality of electric charges. These charges are processed 27 to assemble a digital representation of the biological object. The processing step 27 may be performed on a processor embedded within the scanning device 9 or located externally from the device 9.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. An imaging device comprising:
   a platen;
   an ultrasonic plane wave generator configured to emit a planar-shaped ultrasonic wave;
   an ultrasonic receiver array comprising a plurality of piezoelectric detectors, the receiver array positioned between the platen and the plane wave generator, the receiver array being in physical contact with the platen, the receiver array configured to:
     allow the planar-shaped ultrasonic wave emitted by the plane wave generator to pass through material of the receiver array towards the platen, and
     detect, using the piezoelectric detectors, a reflected portion of the planar-shaped ultrasonic wave; and
   a backer positioned such that the plane wave generator is positioned between the receiver array and the backer, the backer and the platen being arranged as an integral piece to embed the receiver array and the plane wave generator therebetween.

2. The imaging device of claim 1, wherein:
   the plane wave generator is configured to generate and send the ultrasonic wave towards the receiver array, and
   the platen is configured to allow the ultrasonic wave to travel through the platen to reach a biological object in contact with the platen.

3. The imaging device of claim 2, wherein the reflected portion of the ultrasonic wave is reflected from the biological object.

4. The imaging device of claim 1, wherein the backer is configured to absorb acoustic signals associated with the ultrasonic wave.

5. The imaging device of claim 1, wherein the backer is configured to delay acoustic signals associated with the ultrasonic wave.

6. The imaging device of claim 1, wherein the backer comprises a glass material and is fixed by an adhesive to the plane wave generator.

7. The imaging device of claim 1, wherein the platen is bonded to the receiver array.

8. The imaging device of claim 1, wherein the receiver array is a thin film transistor array with a piezoelectric sensing layer.

9. The imaging device of claim 1, wherein the receiver array is a complementary metal-oxide-semiconductor (CMOS) array with a piezoelectric sensing layer.

10. The imaging device of claim 1, wherein the receiver array is a micro-electro-mechanical systems (MEMS) array with a piezoelectric sensing layer.

11. The imaging device of claim 1, wherein the platen includes an acoustic waveguide array.

12. The imaging device of claim 1, wherein the platen includes an acoustic microlens array.

13. An imaging device comprising:
    an ultrasonic plane wave generator configured to transmit a planar-shaped ultrasonic wave;
    an ultrasonic receiver array comprising a plurality of piezoelectric detectors and disposed next to the plane wave generator, the receiver array configured to:
      allow passage of the planar-shaped ultrasonic wave through material of the receiver array, and
      detect, using the piezoelectric detectors, a reflected portion of the planar-shaped ultrasonic wave;
    a platen disposed next to the receiver array and opposite the plane wave generator, the platen fixed to the receiver array, the platen configured to allow passage of the planar-shaped ultrasonic wave through the platen; and
    a backer disposed next to the plane wave generator and opposite the receiver array, the backer and the platen being arranged as an integral piece to embed the receiver array and the plane wave generator therebetween.

14. The imaging device of claim 13, wherein the piezoelectric detectors are an arrangement of detecting elements configured to detect the reflected portion of the ultrasonic wave when reflected from a biological object.

15. The imaging device of claim 14, wherein the detecting elements are arranged in a two-dimensional array addressable by row and column.

16. A method of capturing biometric information comprising:

emitting a substantially planar ultrasonic wave from an ultrasonic plane wave generator, such that the substantially planar ultrasonic wave travels through material of an ultrasonic receiver array positioned between a platen and the plane wave generator before reaching a biological object, the receiver array being in physical contact with the platen;

absorbing or delaying, with a backer arranged with the platen as an integral piece to embed the receiver array and the plane wave generator therebetween, ultrasonic energy from the receiver array;

detecting, with a plurality of piezoelectric detectors of the receiver array, a portion of the ultrasonic wave reflected from the biological object; and converting the detected ultrasonic wave to a plurality of electric charges.

17. The method of claim 16, further comprising processing the plurality of electric charges to assemble a digital image representing the biological object.

18. The method of claim 16, further comprising processing the plurality of electric charges to identify biometric information for the biological object.

19. A method comprising:

transmitting, using an ultrasonic plane wave generator, a planar-shaped ultrasonic wave towards an ultrasonic receiver array positioned between a platen and the plane wave generator, the receiver array allowing passage of the planar-shaped ultrasonic wave through material of the receiver array before reaching a biological object the receiver array being in physical contact with the planten;

absorbing or delaying, using a backer arranged with the platen as an integral piece to embed the receiver array and the plane wave generator therebetween, ultrasonic energy from the receiver array;

detecting, using a plurality of piezoelectric detecting elements of the receiver array, a portion of the ultrasonic wave reflected from the biological object; and processing the detected ultrasonic wave to determine data characterizing the biological object.

* * * * *